United States Patent
Lochtman et al.

(10) Patent No.: US 7,301,034 B2
(45) Date of Patent: Nov. 27, 2007

(54) PREPARATION OF -4-THIOALKYBROBENZENE DERIVATIVES

(75) Inventors: Rene Lochtman, Mannheim (DE); Michael Keil, Freinsheim (DE); Joachim Gebhardt, Wachenheim (DE); Michael Rack, Heidelberg (DE); Wolfgang von Deyn, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 549 days.

(21) Appl. No.: 10/332,861

(22) PCT Filed: Jul. 17, 2001

(86) PCT No.: PCT/EP01/08238

§ 371 (c)(1), (2), (4) Date: Jan. 14, 2003

(87) PCT Pub. No.: WO02/06211

PCT Pub. Date: Jan. 24, 2002

(65) Prior Publication Data

US 2003/0149276 A1    Aug. 7, 2003

(30) Foreign Application Priority Data

Jul. 17, 2000    (DE) ................... 10035075

(51) Int. Cl.
*C07D 261/04*    (2006.01)
*C07D 261/08*    (2006.01)

(52) U.S. Cl. ..................... 548/240; 548/247

(58) Field of Classification Search ................ 548/240, 548/247
See application file for complete search history.

(56) References Cited

FOREIGN PATENT DOCUMENTS

| CA | 2278331 | 7/1998 |
|---|---|---|
| WO | 99/58509 | 11/1990 |
| WO | 98/31681 | 7/1998 |

OTHER PUBLICATIONS

XP-002111134, Oae et al., Bull.Chem.Soc.Jpn.,53, 2023-2026 (1980).

*Primary Examiner*—Rebecca Anderson
(74) *Attorney, Agent, or Firm*—Novak Druce & Quigg, LLP

(57) ABSTRACT

A process for preparing 4-thioalkylbromobenzene derivatives of the formula I

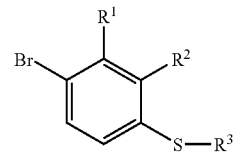

I where:
$R^1$ is $C_1$-$C_6$-alkyl, $C_1$-$C_6$-haloalkyl, $C_1$-$C_6$-alkoxy, $C_1$-$C_6$-haloalkoxy, $C_3$-$C_8$-cycloalkyl, halogen,
$R^2$ is $C_1$-$C_6$-alkyl, $C_1$-$C_6$-alkoxy, $C_3$-$C_8$-cycloalkyl, $C_2$-$C_6$-alkenyl, cyano or a heterocyclic radical,
$R^3$ is $C_1$-$C_6$-alkyl,
which comprises reacting a compound of the formula II,

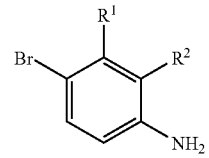

II in which $R^1$ and $R^2$ are as defined above, with a dialkyl disulfide of the formula III $$R^3\text{—S—S—}R^3 \quad \text{III}$$

in the presence of a nitrite and a catalyst in a suitable solvent is described.

13 Claims, No Drawings

PREPARATION OF -4-THIOALKYBROBENZENE DERIVATIVES

This application is a 371 of PCT/EP01/08238 filed Jul. 17, 2001.

The present invention provides a process for preparing 4-thioalkylbromobenzene derivatives.

4-Thioalkylbromobenzene derivatives are useful compounds which are used as intermediates in the chemical industry. They are suitable, for example, for preparing active compounds employed in the field of crop protection, or else for preparing pharmaceutically active compounds or other chemical end products. WO 99/58509, for example, describes—for the case of the plant active compounds—a process for preparing isoxazolin-3-yl-acylbenzenes in which 4-thioalkylbromobenzene derivatives are used as intermediates for preparing plant active compounds. These active compounds (2-alkyl-3-(4,5-dihydroisoxazol-3-yl)acylbenzenes) are described in WO 98/31681 as herbicidally active compounds.

The prior-art processes for preparing 4-thioalkylbromobenzene derivatives, such as the process described in WO 99/58509, are technologically complicated, in particular with respect to the process of the reaction and purification or work-up of the reaction solution. These processes are therefore of limited suitability for the industrial preparation of 4-thioalkylbromobenzene derivatives on a relatively large scale.

It is an object of the present invention to provide an alternative preparation process for these compounds.

We have found that this object is achieved by a process for preparing 4-thioalkylbromobenzene derivatives of the formula I

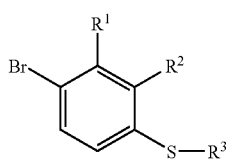

where:
$R^1$ is $C_1$-$C_6$-alkyl, $C_1$-$C_6$-haloalkyl, $C_1$-$C_6$-alkoxy, $C_1$-$C_6$-haloalkoxy $C_3$-$C_8$-cycloalkyl, halogen,
$R^2$ is $C_1$-$C_6$-alkyl, $C_1$-$C_6$-alkoxy, $C_3$-$C_8$-cycloalkyl, $C_2$-$C_6$-alkenyl, cyano or a heterocyclic radical,
$R^3$ is $C_1$-$C_6$-alkyl,
which comprises reacting a compound of the formula II,

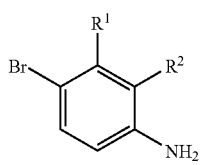

in which $R^1$ and $R^2$ are as defined above, with a dialkyl disulfide of the formula III

in the presence of a nitrite and a catalyst in a suitable solvent.

Surprisingly, the process according to the invention for preparing 4-thioalkylbromobenzene derivatives has, compared to the processes of the prior art, the following advantages: the compounds of the formula I can be obtained both in higher yields and in higher purity than by using the preparation processes of the prior art. Thus, for example, the compound 2-methyl-3,4-dimethylthiobromobenzene can, using the process described in WO 99/58509 (cf. Example 25 therein), only be obtained in a yield of 41%, whereas the yield in the process according to the invention for preparing compounds I is at least 50% or 60%, preferably at least 70% or 80%, especially at least 85%. It is furthermore advantageous that a complicated purification of the reaction solution by filtration of the catalyst can be avoided in the process according to the invention. Compared to the processes of the prior art, a better time and cost efficiency is thus achieved in the preparation of the compounds I. A further advantage in the work-up of the reaction solution consists in the fact that, during purification of the reaction solution by extraction, a considerably better phase separation is achieved by adding water to the organic phase. Phase separation occurs more rapidly, and the phase boundary is markedly better defined than in the processes of the prior art. This likewise results in a higher time and cost efficiency in the preparation of compounds I.

The compounds of the formula I are moreover obtained in higher purity. This is the case in particular when, in the process according to the invention, the compound II is initially charged together with the catalyst in a suitable solvent, and the nitrite is then added continuously or batchwise. This process variant has additional technical advantages. Further improvement of product purity can furthermore be achieved by carrying out the extraction in the further work-up of the product initially with concentrated hydrochloric acid which is diluted with water only for phase separation. Owing to the resulting higher purity of the crude product obtained, it is possible to reduce the overall number of additional purification steps for isolating and working up the compounds I prepared by the process according to the invention. This is particularly advantageous in the large-scale industrial preparation of the compounds I, providing an overall efficient and cost-effective process.

The radicals mentioned above in the definition of $R^1$-$R^3$ have in particular the following meanings:

$C_1$-$C_6$-Alkyl is a straight-chain or branched alkyl group having 1-6 carbons, such as, for example, methyl, ethyl, n-propyl, isopropyl, n-butyl, isobutyl, tert.-butyl, n-pentyl or n-hexyl; preference is given to $C_1$-$C_4$-alkyl, such as, for example, methyl, ethyl, n-propyl, isopropyl, n-butyl, isobutyl or tert.-butyl.

$C_1$-$C_6$-haloalkyl is a straight-chain or branched $C_1$-$C_6$-alkyl group as mentioned above which is partially or fully substituted by fluorine, chlorine, bromine and/or iodine, for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2,-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl; preference is given to $C_1$-$C_4$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2,-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, or nonafluorobutyl;

$C_1$-$C_6$-Alkoxy is a straight-chain or branched alkyl group having 1-6 carbons, such as, for example, methoxy, ethoxy, n-propyloxy, isopropyloxy, n-butyloxy, isobutyloxy, tert.-butyloxy, n-pentyloxy or n-hexyloxy; preference is given to $C_1$-$C_4$-alkoxy, such as, for example, methoxy, ethoxy, n-propyloxy, isopropyloxy, n-butyloxy, isobutyloxy or tert.-butyloxy;

$C_1$-$C_6$-haloalkoxy is a straight-chain or branched $C_1$-$C_6$-alkoxy group as mentioned above which is partially or fully substituted by fluorine, chlorine, bromine and/or iodine, for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2, difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy; preference is given to $C_1$-$C_4$-haloalkoxy, such as fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2, difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, or nonafluorobutoxy;

$C_3$-$C_8$-cycloalkyl is an unsubstituted or substituted cycloalkyl ring having 3-8 carbons, such as, for example, cyclopropyl, cyclobutyl, cyclopentyl, cyclohexyl, cycloheptyl or cyclooctyl. Suitable substituents are, for example: $C_1$-$C_6$-alkyl, $C_1$-$C_6$-alkoxy or halogen; preference is given to $C_3$-$C_6$-cycloalkyl, which is unsubstituted, such as, for example cyclopropyl, cyclopentyl or cyclohexyl;

$C_2$-$C_6$-alkenyl is a straight-chain or branched alkenyl group having 2-6 carbon atoms, wherein the double bond is located at the connecting position, such as for example ethenyl, prop-1-en-1-yl, 1-methylethenyl, buten-1-yl, 1-methylprop-1-en-1-yl, 2-methylprop-1-en-1-yl, penten-1-yl, 1-methyl-but-1-en-1-yl, 2-methylbut-1-en-1-yl, 3-methylbut-1-en-1-yl, 1,2-dimethylprop-1-en-1-yl, hex-1-en-1-yl, 1-methylpent-1-en-1-yl, 2-methylpent-1-en-1-yl, 3-methylpent-1-en-1-yl, 4-methylpent-1-en-1-yl, 1,2-dimethylbut-1-en-1-yl, 1,3-dimethylbut-1-en-1-yl, 2,3-dimethylbut-1-en-1-yl, 3,3-dimethylbut-1-en-1-yl, 1-ethylbut-1-en-1-yl, 2-ethylbut-1-en-1-yl or 1-ethyl-2-methylprop-1-en-1-yl;

Halogen is fluorine, chlorine, bromine, in particular chlorine or bromine.

"Heterocyclic ring" is a saturated, unsaturated or partially unsaturated heterocycle having 3-8 ring atoms and one, two or three oxygen, sulfur or nitrogen atoms. Preference is given to heterocycles which contain at least one oxygen and/or one nitrogen atom. Preference is furthermore given to heterocycles having 5 or 6 ring atoms. The heterocycle can be attached to the phenyl ring via any site on the heterocycle, for example via a heterocyclic nitrogen ring atom or a carbon ring atom. The heterocycles are unsubstituted or mono-, di- or trisubstituted. Suitable substituents are radicals which are chemically inert under the chosen reaction conditions, such as, for example, $C_1$-$C_6$-alkyl, $C_1$-$C_6$-alkoxy or halogen. Heterocyclic rings suitable for the purpose of the present invention are, for example, the following heterocycles: pyrrolyl, pyrazolyl, imidazolyl, oxazolyl, isoxazolyl, thiazolyl, thiadiazolyl, piperidinyl, morpholinyl, oxazinyl, isoxazolinyl, isoxazolidinyl, etc. Preference is given to the following heterocycles: isoxazolyl, isoxazolinyl or isoxazolidinyl, in particular 4,5-dihydroisoxazol-3-yl or 4,5-dihydroisoxazol-5-yl.

The process according to the invention is preferably suitable for preparing compounds of the formula I, wherein the meaning of the substituents is as follows:
$R^1$ $C_1$-$C_6$-alkyl, $C_1$-$C_6$-alkoxy, $C_3$-$C_8$-cycloalkyl, halogen;
$R^2$ $C_1$-$C_6$-alkyl, $C_1$-$C_6$-alkoxy, $C_3$-$C_8$-cycloalkyl, cyano or a heterocyclic radical;
$R^3$ $C_1$-$C_6$-alkyl.

The process according to the invention is preferably suitable for preparing compounds of the formula I, wherein the meaning of the substituent $R^3$ is $C_1$-$C_4$-alkyl, preferably $C_1$-$C_2$-alkyl, especially methyl.

The process according to the invention is preferably suitable for preparing the following compounds of the formula I:
4-methylthio-3-(4,5-dihydroisoxazol-3-yl)-2-methylbromobenzene
4-methylthio-3-(4,5-dihydroisoxazol-3-yl)-2-ethylbromobenzene
4-methylthio-3-(4,5-dihydroisoxazol-3-yl)-2-methoxybromobenzene
4-methylthio-3-(4,5-dihydroisoxazol-3-yl)-2-ethoxybromobenzene
4-methylthio-3-(3-methyl-4,5-dihydroisoxazol-5-yl)-2-methylbromobenzene
4-methylthio-3-(3-methyl-4,5-dihydroisoxazol-5-yl)-2-ethylbromobenzene
4-methylthio-3-(3-methyl-4,5-dihydroisoxazol-5-yl)-2-methoxybromobenzene
4-methylthio-3-(3-methyl-4,5-dihydroisoxazol-5-yl)-2-ethoxybromobenzene
4-methylthio-3-(isoxazol-3-yl)-2-methylbromobenzene
4-methylthio-3-(isoxazol-3-yl)-2-ethylbromobenzene
4-methylthio-3-(isoxazol-3-yl)-2-methoxybromobenzene 4-methylthio-3-(isoxazol-3-yl)-2-ethoxybromobenzene
4-methylthio-3-(5-methylisoxazol-3-yl)-2-methylbromobenzene
4-methylthio-3-(5-methylisoxazol-3-yl)-2-ethylbromobenzene
4-methylthio-3-(5-methylisoxazol-3-yl)-2-methoxybromobenzene
4-methylthio-3-(5-methylisoxazol-3-yl)-2-ethoxybromobenzene
4-methylthio-3-cyanobromobenzene
4-methylthio-3-cyano-2-methylbromobenzene The reaction of the compounds II with the compounds III is carried out, for example, using the following process steps:

The compound II, if appropriate together with the disulfide III, a catalyst, is initially charged as a solution or suspension in a suitable solvent or solvent mixture, and the nitrite is then added batchwise or continuously. In a preferred embodiment, the compound II and the disulfide, which simultaneously serves as solvent, are initially charged. After the reaction has ended, the reaction solution is worked up by removing the catalyst. Removal of the catalyst is preferably carried out by extraction with inorganic acids, for example hydrochloric acid or sulfuric acid.

Particularly suitable catalysts are copper powder and inorganic or organic mono- or divalent copper salts, such as, for example, copper chlorides, copper bromides or copper sulfate. Preference is given to using copper powder.

Suitable nitrites are organic $C_1$-$C_6$-alkyl nitrites, for example n-butyl nitrite, (iso)amyl nitrite or tert-butyl nitrite, or $C_1$-$C_6$-alkyl dinitrites, for example ethylens glycole dinitrite, or nitrite salts from the group of the alkali metals or alkaline earth metals, such as sodium nitrite or potassium nitrite. Preference is given to organic $C_1$-$C_6$-alkyl nitrites or nitrite salts form the group of the alkali metals or alkaline earth metals. In a particular embodiment, the nitrite used is a $C_1$-$C_6$-alkyl nitrite, for example n-butyl nitrite, (iso)amyl nitrite or tert.-butyl nitrite. In another particular embodiment, the nitrite used is a alkali metal nitrite, for example sodium nitrite.

The reaction of compounds II with disulfides III in the presence of nitrites is carried out in suitable inert solvents or solvent mixtures, such as dimethyl disulfide, esters of acetic acid, for example ethyl acetate; aromatic compounds, for example benzene, toluene, chlorobenzene or nitrobenzene; halogenated alkanes, for example methylene chloride or 1,2-dichloroethane. Particular preference is given to dimethyl disulfide.

The reaction is carried out at temperatures of from room temperature to the boiling point of the solvent, in particular from 30 to 100° C., preferably at from 50 to 80° C., in particular at from 55 to 75° C.

In a particular embodiment, the catalyst used is elemental copper. In this case, the copper is advantageously removed from the reaction solution by adding inorganic or organic acids, for example hydrochloric acid or sulfuric acid. After the compound II has reacted with the dialkyldisulfide III, the required amount of an acid is added and the mixture is stirred until the catalyst has substantially been dissolved. In this manner, the complicated removal of the catalyst from the reaction solution by filtration can be avoided.

The reaction time for the reaction of compounds II with disulfides III is 1-12 hours, preferably 2-8 hours.

After removal of the catalyst, the product can be isolated by removing the solvent and low-boiling components by distillation or concentration under reduced pressure. Preference is given to complete removal of the solvents by distillation. It is then possible to use the crude product as a melt in further steps in the context of the further reaction for preparing active compounds or corresponding intermediates, or to purify the product in an appropriate manner.

In a preferred embodiment, the reagent used for the reaction of compounds II with dialkyl disulfides are alkali metal nitrites or alkaline earth metal nitrites in the presence of mineral acids. To this end, the compound II is initially charged together with the disulfide III, a catalyst and, if appropriate, a solvent, and the mixture is stirred for from 15 minutes to four hours, preferably from 15 minutes to two hours. Particular preference is given to a variant where the disulfide III serves simultaneously as solvent, and no other solvents are used. An aqueous nitrite solution is then added at 20° C.-80° C., preferably at 40° C.-60° C. Preference is given to using solutions of sodium nitrite or potassium nitrite. A mineral acid, preferably concentrated hydrochloric acid or sulfuric acid, is then added at 20° C.-80° C., preferably at 50° C.-75° C. The reaction time is 1-12 hours, preferably 2-8 hours. Work-up is carried out, for example, by extraction with concentrated or dilute mineral acids, such as hydrochloric acid or sulfuric acid, preferably concentrated hydrochloric acid.

In another preferred embodiment, the reagent used for the reaction of compounds II with dialkyl disulfides are organic $C_1$-$C_6$-alkylnitrites, for example n-butyl nitrite, (iso)amylnitrite or tert.-butylnitrite. To this end, the compound II is initially charged together with the disulfide III, a catalyst and, if appropriate, a solvent, and the mixture is stirred up to four hours, preferably up to two hours. Particular preference is given to a variant where the disulfide III serves simultaneously as solvent, and no other solvents are used. The $C_1$-$C_6$-alkyl nitrite and, if appropriate, a solvent, for example the disulfide III, is then added at 20° C.-80° C., preferably at 40° C.-70° C., especially 55° C.-70° C. Preference is given to add the $C_1$-$C_6$-alkyl nitrite without a solvent. The reaction time is 0.5-12 hours, preferably 1-8 hours, especially 1-6 hours. Then the reaction mixture is cooled to room temperature. Work-up is carried out, for example, by extraction with concentrated or dilute mineral acids, such as hydrochloric acid or sulfuric acid, preferably concentrated hydrochloric acid.

Further purification of the crude product is carried out either by washing the residue obtained or by crystallization. Suitable for washing are, for example, water or water-miscible solvents or hydroxide solutions, like sodiumhydroxide. Suitable for recrystallization are, for example, toluene or benzene.

In principle, the resulting crude product can also be employed without further purification of the reaction solution for the next reaction step in the context of the further conversion for preparing active compounds. To this end the reaction solution, which contains compounds of the formula I, can be diluted with further solvents and in this manner be used as a crude solution for the next step of the process. Alternatively, it is also possible to concentrate the reaction solution and to transfer the resulting residue directly or as a melt into the next step of the process.

In a preferred embodiment of the process, the compound of the formula II and the nitrite are employed in a molar ratio of 1:0.8 to 1:1.5. The nitrite is preferably employed in about equimolar amounts, or in a slight excess (up to about 5 mol %).

In a preferred embodiment of the process the dialkyl disulfide of the formula III is used in excess with regard to the compound of formula II. Especially the dialkyl disulfide of the formula II is used as a solvent.

In a preferred embodiment of the process the catalyst and the compound of formula II are employed in a molar ratio of from 0.005:1 to 0.05:1, especially from 0.01:1 to 0.02:1.

The compounds of the formula II to be used as starting materials are known from the literature and/or commercially available. They can also be prepared by processes known per se, as described in more detail in WO 98/31681 or WO 99/58509, for example.

The invention is illustrated in more detail in the embodiments below.

EXAMPLE 1

3-(3-Bromo-2-methyl-6-methylthiophenyl)-4,5-dihydroisoxazole 114.7 g (0.45 mol) of 4-bromo-2-(4,5-dihydroisoxazol-3-yl)-3-methylaniline, 857 mg of copper powder and 1000 ml of dimethyl disulfide are initially charged. Over a period of one hour, 49.2 g of n-butyl nitrite are metered in at 58-65° C., and the mixture is stirred until the reaction has gone to completion (about 1-3 hours). At 20-25° C., 130 ml of conc. hydrochloric acid are added, and the mixture is stirred for 20-30 minutes. 130 ml of water are added, and the phases are then separated. Washing is repeated twice. The organic phase is concentrated, giving 114.4 g of product (yield: 89%).

EXAMPLE 2

3-(3-Bromo-2-methyl-6-methylthiophenyl)-4,5-dihydroisoxazole 10 g (35.3 mmol) of 4-bromo-2-(4,5-dihydroisoxazol-3-yl)-3-methylaniline, 67.3 mg of copper powder and 58.5 ml of dimethyl disulfide are initially charged, and the mixture is stirred for one hour. At 50° C., 9.05 g of a 40.4% strength aqueous sodium nitrite solution are added. At 63-65° C., 6.96 g of 25% strength sulfuric acid are then metered in, and the mixture is stirred at 65° C. for 3 hours. At 20-25° C., 15 ml of conc. hydrochloric acid are added, and the mixture is stirred for one hour. 15 ml of water are added, and the phases are then separated. Washing is repeated twice. The organic phase is concentrated, giving 6.7 g of a brown solid (yield: 58%).

We claim:

1. A process for preparing 4-thioalkylbromobenzene derivatives of the formula I

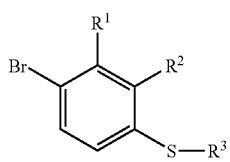

where:
$R^1$ is $C_1$-$C_6$-alkyl, $C_1$-$C_6$haloalkyl, $C_1$-$C_6$alkoxy, $C_1$-$C_6$haloalkoxy, $C_3$-$C_8$-cycloalkyl, halogen, $R^2$ is isoxazole, isoxazoline or isoxazolidine,
$R^3$ is $C_1$-$C_6$alkyl;
which comprises reacting a compound of the formula II,

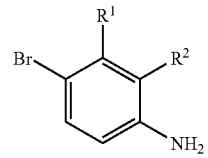

in which $R^1$ and $R^2$ are as defined above, with a dialkyl disulfide of the formula III

in the presence of a nitrite and a catalyst in a suitable solvent, and wherein, the catalyst and the compound of formula II are employed in a molar ratio of from 0.005:1 to 0.05:1.

2. A process as claimed in claim 1, wherein the catalyst used is copper powder.

3. A process as claimed in claim 2, wherein the copper powder is removed from the reaction solution by adding an acid.

4. A process as claimed in claim 1, wherein the solvent used is the dialkyl disulfide of the formula III.

5. A process as claimed in claim 1, wherein the reaction is carried out at temperatures of from 30 to 100° C.

6. A process as claimed in claim 1, wherein the reaction is carried out in the presence of sodium nitrite and sulfuric acid.

7. A process as claimed in claim 1, wherein the reaction is carried out in the presence of a $C_1$-$C_6$-alkyl nitrite.

8. A process as claimed in claim 1, wherein $R^1$ is $C_1$-$C_6$-alkyl.

9. A process as claimed in claim 8, wherein $R^1$ is methyl or ethyl.

10. A process as claimed in claim 1 for preparing the following compounds:
4-methylthio-3-(4, 5-dihydroisoxazol-3-yl) -2-methylbromobenzene
4-methylthio-3-(4, 5-dihydroisoxazol-3-yl) -2-etbylbromobenzene
4-methylthio-3-(4, 5-dibydroisoxazol-3-yl) -2-methoxybromobenzene
4-methylthio-3-(4, 5-dihydroisoxazol-3-yl) -2-ethoxybromobenzene
4-methylthio-3-(3-methyl-4, 5-dihydroisoxazol-5-yl)-2-methyl-bromobenzene
4-methylthio-3-(3-methyl-4, 5-dihydroisoxazol-5-yl)-2-ethylbromobenzene
4-methylthio-3-(3-methyl-4, 5-dihydroisoxazol-5-yl)-2-methoxybromobenzene
4-methylthio-3-(3-methyl-4, 5-dihydroisoxazol-5-yl)-2-ethoxybromobenzene
4-methylthio-1-(isoxazol-3-yl)-2-methylbromobenzene
4-methylthio-3-(isoxazol-3-yl)-2-ethylbromobenzene
4-methylthio-3-(isoxazol-3-yl)-2-methoxybromobenzene
4-methylthio-3-(isoxazol-3-yl)-2-ethoxybromobenzene
4-methylthio-3-(5-methylisoxazol-3-yl)-2-methylbromobenzene
4-methylthio-3-(5-methylisoxazol-3-yl)-2-ethylbromobenzene 4-metbylthio-3-(5-methylisoxazol-3-yl)-2-methoxybromobenzene 4-methylthio-3-(5-methylisoxazol-3-yl)-2-ethoxybromobenzene.

11. A process as claimed in claim 10 for preparing 4methylthio-3-(4, 5dihydroisoxazol3-yl) -2-methylbromobenzene.

12. A process as claimed in claim 1, wherein the molar ratio of the catalyst to the compound of formula II is from 0.01:1 to 0.05:1.

13. A process as claimed in claim 1, wherein the molar ratio of the catalyst to the compound of formula II is from 0.01:1 to 0.02:1.

* * * * *

UNITED STATES PATENT AND TRADEMARK OFFICE
CERTIFICATE OF CORRECTION

PATENT NO. : 7,301,034 B2
APPLICATION NO. : 10/332861
DATED : November 27, 2007
INVENTOR(S) : Lochtman et al.

It is certified that error appears in the above-identified patent and that said Letters Patent is hereby corrected as shown below:

Claim 1, col. 7, line 66: "$C_1$-$C_6$haloalkyl" should read --$C_1$-$C_6$-haloalkyl--
Claim 1, col. 7, line 66: "$C_1$-$C_6$alkoxy" should read --$C_1$-$C_6$-alkoxy--
Claim 1, col. 7, line 67: "$C_1$-$C_6$haloalkoxy" should read --$C_1$-$C_6$-haloalkoxy--
Claim 1, col. 8, line 2: "$C_1$-$C_6$alkyl" should read --$C_1$-$C_6$-alkyl--
Claim 1, col. 8, line 19: "and wherein, the" should read --and wherein the--
Claim 10, col. 8, line 45: "4-methylthio-3-(4, 5-dihydroisoxazol-3-yl)-2-etbylbromobenzene" should read --4-methylthio-3-(4,5-dihydroisoxazol-3-yl)-2-ethylbromobenzene--
Claim 10, col. 8, line 47: "4-methylthio-3-(4, 5-dibyroisoxazol-3-yl)-2-methoxybromobenze" should read --4-methylthio-3-(4,5-dihyroisoxazol-3-yl)-2-methoxybromobenze--
Claim 10, col. 8, line 51: "4-methylthio-3-(3-methyl-4, 5-dihydroisoxazol-5-yl)-2-methyl-bromobenzene" should read --4-methylthio-3-(3-methyl-4,5-dihydroisoxazol-5-yl)-2-methylbromobenzene--
Claim 10, col. 8, line 55: "4-methylthio-3-(3-methyl-4, 5-dihydroisoxazol-5-yl)-2-methyloxybromobenzene" should read --4-methylthio-3-(3-methyl-4,5-dihydroisoxazol-5-yl)-2-methyloxybromobenzene--
Claim 10, col. 8, line 57: "4-methylthio-3-(3-methyl-4, 5-dihydroisoxazol-5-yl)-2-ethyloxybromobenzene" should read --4-methylthio-3-(3-methyl-4,5-dihydroisoxazol-5-yl)-2-ethyloxybromobenzene--

UNITED STATES PATENT AND TRADEMARK OFFICE
CERTIFICATE OF CORRECTION

PATENT NO. : 7,301,034 B2
APPLICATION NO. : 10/332861
DATED : November 27, 2007
INVENTOR(S) : Lochtman et al.

It is certified that error appears in the above-identified patent and that said Letters Patent is hereby corrected as shown below:

Claim 10, col. 8, line 60: "4-methylthio-1-(isoxaol-3-yl)-2-methylbromobenzene" should read --4-methylthio-3-(isoxaol-3-yl)-2-methylbromobenzene--
Claim 10, col. 9, line 1: "4-metbylthio" should read --4-methylthio--
Claim 11, col. 9, line 6: "4methylthio-3-(4, 5dihydroisoxazol3-yl) -2-methylbromobenzene" should read --4-methylthio-3-(4,5-dihydroisoxazol-3-yl) -2-methylbromobenzene--

Signed and Sealed this

Fifteenth Day of April, 2008

JON W. DUDAS
*Director of the United States Patent and Trademark Office*